US009359187B2

(12) United States Patent
Bodanewse et al.

(10) Patent No.: US 9,359,187 B2
(45) Date of Patent: Jun. 7, 2016

(54) OFFSHORE FLUID OFFLOADING SYSTEMS AND METHODS

(75) Inventors: Luiz Germano Bodanewse, Rio de Janeiro (BR); James V. Maher, Houston, TX (US); Ricky Carl Brown, Cat Spring, TX (US)

(73) Assignee: HORTON DO BRASIL TECHNOLOGIA OFFSHORE, LTDA., Houston, TX (US)

( * ) Notice: Subject to any disclaimer, the term of this patent is extended or adjusted under 35 U.S.C. 154(b) by 1013 days.

(21) Appl. No.: 13/208,789

(22) Filed: Aug. 12, 2011

(65) Prior Publication Data
US 2012/0037265 A1 Feb. 16, 2012

Related U.S. Application Data

(60) Provisional application No. 61/373,649, filed on Aug. 13, 2010.

(51) Int. Cl.
*B67D 9/00* (2010.01)
*B63B 35/44* (2006.01)
(Continued)

(52) U.S. Cl.
CPC . *B67D 9/00* (2013.01); *B63B 27/34* (2013.01); *B65H 75/38* (2013.01); *B65H 75/4402* (2013.01); *B65H 75/4415* (2013.01); *B65H 75/4486* (2013.01); *B63B 22/026* (2013.01); *B63B 2035/442* (2013.01); *B63B 2035/448* (2013.01); *B65H 2701/33* (2013.01)

(58) Field of Classification Search
CPC .......... B67D 9/00; B63B 35/44; B63B 22/00; B63B 27/34; B63B 22/02; B65H 75/48; B65H 57/00; B65H 49/20

USPC .............. 141/1, 387; 441/5; 114/45, 264; 166/350, 351, 352, 353, 354, 355, 359
See application file for complete search history.

(56) References Cited

U.S. PATENT DOCUMENTS 2,903,716 A * 9/1959 Zasada ................ B63B 22/02
441/21
3,055,336 A * 9/1962 Cook .................. B63B 22/02
114/230.28
(Continued)

FOREIGN PATENT DOCUMENTS

EP 49549 A1 * 4/1982 ............ B63B 35/44
JP 10-168854 6/1998

OTHER PUBLICATIONS

English Translation of Abstract of JP10-168854 (1 page).
(Continued)

*Primary Examiner* — Mark A Laurenzi
*Assistant Examiner* — Andrew Schmid
(74) *Attorney, Agent, or Firm* — Conley Rose, P.C.

(57) ABSTRACT

A system for offloading a fluid from an offshore structure comprises an annular conduit support structure disposed about the offshore structure. The support structure is fixably coupled to the offshore structure. In addition, the system comprises an annular reel disposed about the offshore structure and rotatably coupled to the support structure. The reel includes a conduit fairlead configured to move relative to the support structure. Further, the system comprises a flexible conduit having a fluid inlet end and a fluid outlet end. The flexible conduit includes a first portion wrapped around the conduit support structure and a second portion extending from the conduit support structure through the fairlead.

21 Claims, 9 Drawing Sheets

(51) Int. Cl.
*B63B 27/34* (2006.01)
*B65H 75/38* (2006.01)
*B65H 75/44* (2006.01)
*B63B 22/02* (2006.01)

(56) References Cited

U.S. PATENT DOCUMENTS

| | | | | |
|---|---|---|---|---|
| 3,062,169 A * | 11/1962 | Cook | B63B 22/02 | 114/230.28 |
| 3,074,082 A * | 1/1963 | Griebe | B63B 22/021 | 114/230.12 |
| 3,155,069 A * | 11/1964 | Ross | B63B 21/50 | 114/230.19 |
| 3,247,674 A * | 4/1966 | Macardier | B63B 1/041 | 242/362 |
| 3,315,630 A * | 4/1967 | Hopkins | B63B 22/021 | 114/230.26 |
| 3,349,816 A * | 10/1967 | Mowell | B63B 22/021 | 137/236.1 |
| 3,372,461 A * | 3/1968 | Tesson | F16L 1/203 | 228/155 |
| 3,430,670 A * | 3/1969 | Hopkins | B63B 22/025 | 137/236.1 |
| 3,464,466 A * | 9/1969 | Bryan | B63B 22/021 | 114/230.12 |
| 3,519,036 A * | 7/1970 | Manning | B63B 22/021 | 114/257 |
| 3,568,737 A * | 3/1971 | Burns | B65D 88/78 | 114/257 |
| 3,742,536 A * | 7/1973 | Sada | B63B 22/021 | 137/236.1 |
| 3,774,253 A * | 11/1973 | Lecomte | B63B 22/021 | 114/230.13 |
| 3,913,157 A * | 10/1975 | Versluis | B63B 22/021 | 137/236.1 |
| 4,117,692 A * | 10/1978 | Oberg | B63B 35/03 | 405/158 |
| 4,130,076 A * | 12/1978 | van Bilderbeek | B63B 22/021 | 441/133 |
| 4,176,615 A * | 12/1979 | Reid | B63B 22/021 | 441/133 |
| 4,270,611 A * | 6/1981 | Arnaudeau | B63B 22/021 | 141/387 |
| 4,315,533 A * | 2/1982 | Eagles | B67D 9/02 | 137/615 |
| 4,448,568 A * | 5/1984 | Gentry | B63B 22/021 | 166/345 |
| 4,480,575 A * | 11/1984 | Delamare | B63B 22/021 | 114/230.15 |
| 4,597,595 A * | 7/1986 | Wallace | B63B 22/021 | 141/387 |
| 4,643,462 A * | 2/1987 | Wallace | B63B 27/24 | 141/387 |
| 4,735,167 A * | 4/1988 | White | B63B 22/021 | 114/230.14 |
| 4,867,211 A * | 9/1989 | Dodge | B63B 27/24 | 137/615 |
| 4,915,416 A * | 4/1990 | Barrett | B63B 22/021 | 141/387 |
| 5,531,246 A * | 7/1996 | Ritter | B65H 75/425 | 137/355.16 |
| 5,547,314 A * | 8/1996 | Ames | E21B 7/128 | 166/346 |
| 7,322,308 B2 * | 1/2008 | De Baan | B63B 21/50 | 114/230.1 |
| 7,681,830 B2 * | 3/2010 | Tsuruta | B65B 9/20 | 242/554.3 |
| 8,561,563 B2 * | 10/2013 | Yao | B63B 21/50 | 114/230.13 |
| 2004/0134662 A1 * | 7/2004 | Chitwood | E21B 4/04 | 166/367 |
| 2005/0087644 A1 * | 4/2005 | Kim | B65H 75/425 | 242/390.8 |
| 2006/0273213 A1 * | 12/2006 | Turk | B65H 75/425 | 242/397.3 |
| 2007/0155260 A1 * | 7/2007 | Poldervaart | B63B 22/021 | 441/5 |
| 2008/0214072 A1 * | 9/2008 | Saint-Marcoux | B63B 21/508 | 441/5 |
| 2010/0326667 A1 * | 12/2010 | Coppens | B63B 27/24 | 166/355 |
| 2011/0107951 A1 * | 5/2011 | Vandenworm | B63B 1/041 | 114/125 |
| 2011/0253023 A1 * | 10/2011 | Tahar | B63B 35/4413 | 114/264 |
| 2012/0037265 A1 * | 2/2012 | Bodanese | B63B 27/34 | 141/1 |
| 2012/0260839 A1 * | 10/2012 | Maher | B65D 90/02 | 114/257 |
| 2013/0233224 A1 * | 9/2013 | Bodanese | B63B 9/065 | 114/45 |
| 2013/0279990 A1 * | 10/2013 | Nygaard | B63B 27/34 | 405/195.1 |
| 2014/0008076 A1 * | 1/2014 | Skaugen | E21B 17/015 | 166/367 |

OTHER PUBLICATIONS

International Search Report and Written Opinion for PCT/US2011/047593 dated Feb. 22, 2012 (9 pages).

ARIPO Examination Report dated Oct. 8, 2015 for ARIPO Application No. AP/P/2013/006758 (6 p.).

* cited by examiner

OFFSHORE FLUID OFFLOADING SYSTEMS AND METHODS

CROSS-REFERENCE TO RELATED APPLICATIONS

This application claims benefit of U.S. provisional patent application Ser. No. 61/373,649 filed Aug. 13, 2010, and entitled "Flexible Riser Offloading System," which is hereby incorporated herein by reference in its entirety.

STATEMENT REGARDING FEDERALLY SPONSORED RESEARCH OR DEVELOPMENT

Not applicable.

BACKGROUND

1. Field of the Invention

This disclosure relates generally to a system for offloading oil from an offshore Floating Production Storage and Offloading Unit (FPSO) or Floating Storage and Offloading Unit (FSO). More particularly, it relates to an apparatus, systems, and methods for mooring an offloading vessel to an offshore FPSO or FSO.

2. Background of the Technology

Floating Production Storage and Offloading units (FPSOs) and Floating Storage and Offloading Units (FSOs) are commonly used in offshore oil and gas operations to temporarily store and then offload produced oil. An FPSO vessel is designed to receive crude oil produced from a nearby platform or subsea template, process the crude oil (e.g., separation of water from the crude oil), and store the processed oil until it can be offloaded to a tanker or transported through a pipeline. An FSO vessel is a simplified FPSO without the ability to process crude oil. An FSO typically receives and stores oil that has already been processed, and then offloads the stored oil to a tanker or through a pipeline. FPSOs and FSOs are particularly suited in frontier offshore regions where there is no pipeline infrastructure in place for transporting produced oil to the shore. In particular, the FPSO/FSO is employed to store the produced oil until it can be offloaded for transport to another location.

Typically, FPSOs and FSOs are ship-shaped floating vessels or barges that are moored to the sea floor. A plurality of production lines and a plurality of offloading lines are connected to a turret mounted to the bow of the FPSO/FSO. The production lines supply oil to the FPSO/FSO and the offloading lines offload oil stored in the FPSO/FSO to a tanker. A mooring system connects the turret to the sea floor, thereby mooring the FPSO/FSO. In some cases, a hawser also connects to the turret to moor another offshore vessel to the FPSO/FSO. Thus, the turret provides a strongpoint and mounting unit for mooring the FPSO/FSO, while also providing a structural support for the supply lines and the offloading lines. As such, a turret is an important, but complex and expensive component of a conventional FPSO/FSO. For some deepwater applications, the design parameters of the turret may need to be extremely large, bordering on concept feasibility.

There are a few different ways to offloading a moored FPSO/FSO. One approach is to utilize an offloading buoy that is moored to the sea floor and connected to one or more of the offloading lines of the FPSO/FSO. An offloading tanker moors itself to the buoy and weathervanes about the buoy. A conduit extends from the tanker to the buoy and offloads oil supplied to the buoy via the FPSO/FSO offloading line. Since this method employs two floating structures moored to the sea floor (i.e., the FPSO/FSO and the buoy), it can be relatively complex and expensive to implement. Further, since offloading lines extend between the buoy and the FPSO/FSO and the tanker weathervanes about the buoy, there is a possibility of the tanker (or conduits extending between the tanker and the buoy) interfering with the FPSO/FSO (or the offloading lines extending from the FPSO/FSO and the buoy).

Another conventional approach is to directly connect one or more flexible offloading lines of the moored FPSO/FSO to a tanker. The tanker may be moored to the FPSO/FSO with a hawser connected to the turret of the FPSO/FSO and allowed to weathervane about the FPSO/FSO, or the tanker may maintain its position with a dynamic positioning system (DPS). This approach eliminates the need for a second structure moored to the sea floor (i.e., offloading buoy), but has its own set of unique challenges. Specifically, regarding the first method, the turret must be designed to allow the offloading lines to pivot or rotate as the tanker weathervanes. This added functionality may increase the complexity, and associated cost, of the turret. For the second method, the tanker must be equipped with a DPS, which typically includes a global positioning system mated with a plurality of thrusters that work together to maintain the tanker in a specific position for offloading. However, some of the larger tankers such as Very Large Crude Carrier (VLCC) tankers are typically not outfitted with a DPS, and therefore, may not be suitable for offloading in this manner.

Accordingly, there remains a need in the art for improved systems and methods for offloading oil from an FPSO or FSO. Such systems and methods would be particularly well-received if they eliminated the need for DPS, and thus, were suited for use with VLCC tankers, and/or did not require the use of a turret.

BRIEF SUMMARY OF THE DISCLOSURE

These and other needs in the art are addressed in one embodiment by a system for offloading a fluid from an offshore structure. In an embodiment, the system comprises annular conduit support structure disposed about the offshore structure. The support structure is fixably coupled to the offshore structure. In addition, the system comprises an annular reel disposed about the offshore structure and rotatably coupled to the support structure. The reel includes a conduit fairlead configured to move relative to the support structure. Further, the system comprises a flexible conduit having a fluid inlet end and a fluid outlet end. The flexible conduit includes a first portion wrapped around the conduit support structure and a second portion extending from the conduit support structure through the fairlead.

These and other needs in the art are addressed in another embodiment by a method for offloading a fluid from an offshore structure to a tanker. In an embodiment, the method comprises (a) winding a flexible conduit about the offshore structure. In addition, the method comprises (b) connecting a fluid inlet end of the flexible conduit to a fluid outlet of the offshore structure. Further, the method comprises (c) pulling a fluid outlet end of the flexible conduit from the offshore structure. Still further, the method comprises (d) unwinding at least a portion of the flexible conduit from the offshore structure during (c). Moreover, the method comprises a (e) connecting the outlet end of the flexible conduit to the tanker.

These and other needs in the art are addressed in another embodiment by a system. In an embodiment, the system comprises a floating offshore structure moored to the sea floor with a plurality of mooring lines. In addition, the system comprises a tanker spaced apart from the offshore structure. Further, the system comprises a flexible conduit extending from the offshore structure to the tanker, wherein the conduit has an inlet end coupled to the offshore structure, an outlet end pivotally coupled to the tanker, a first portion extending from the inlet end, and a second portion extending from the first portion and the offshore structure to the outlet end. The first portion is coiled around the offshore structure.

Embodiments described herein comprise a combination of features and advantages intended to address various shortcomings associated with certain prior devices, systems, and methods. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
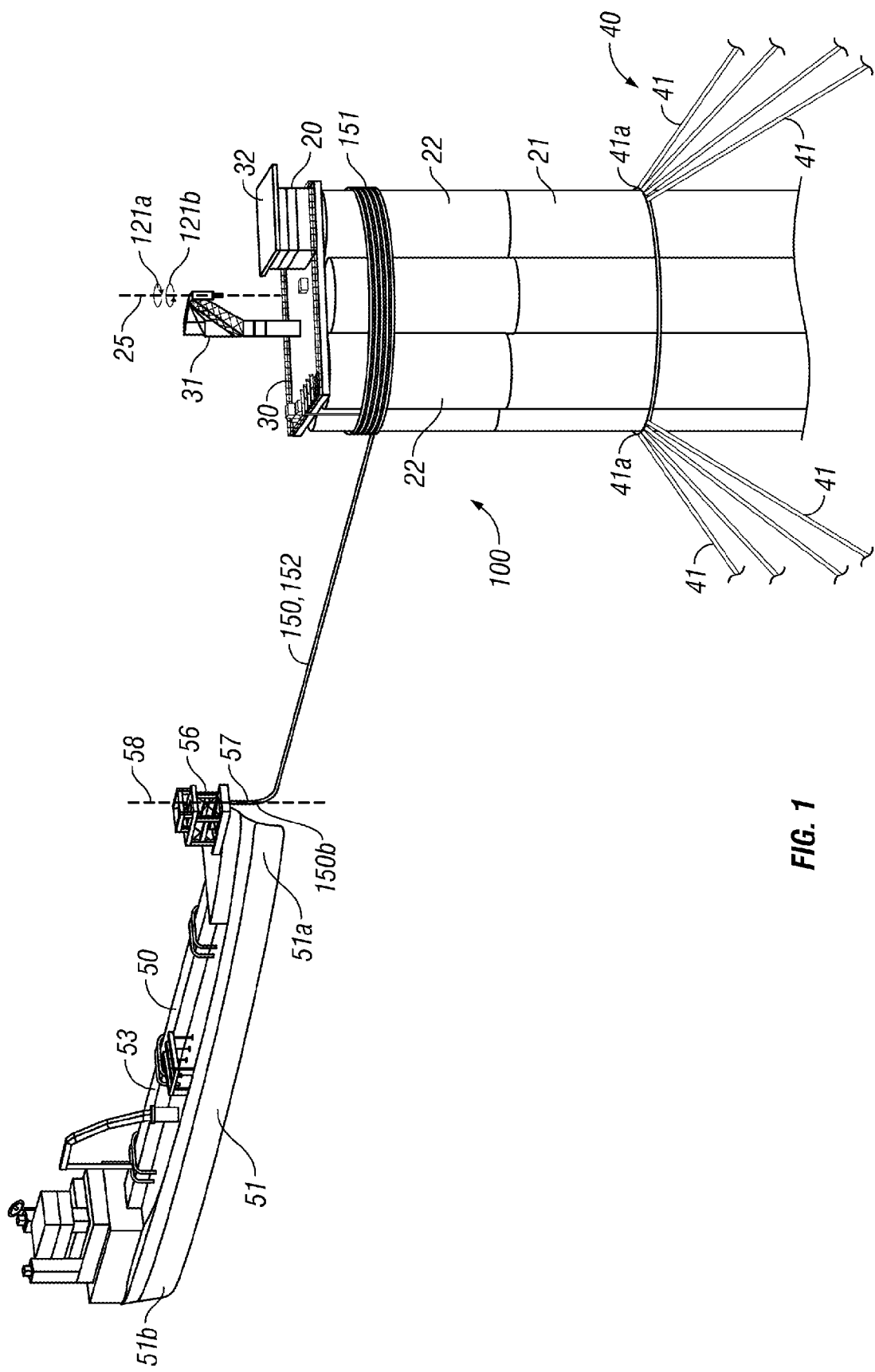
FIG. 1 is a perspective side view of a system for the offshore transfer of a stored fluid.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

Figure 2:
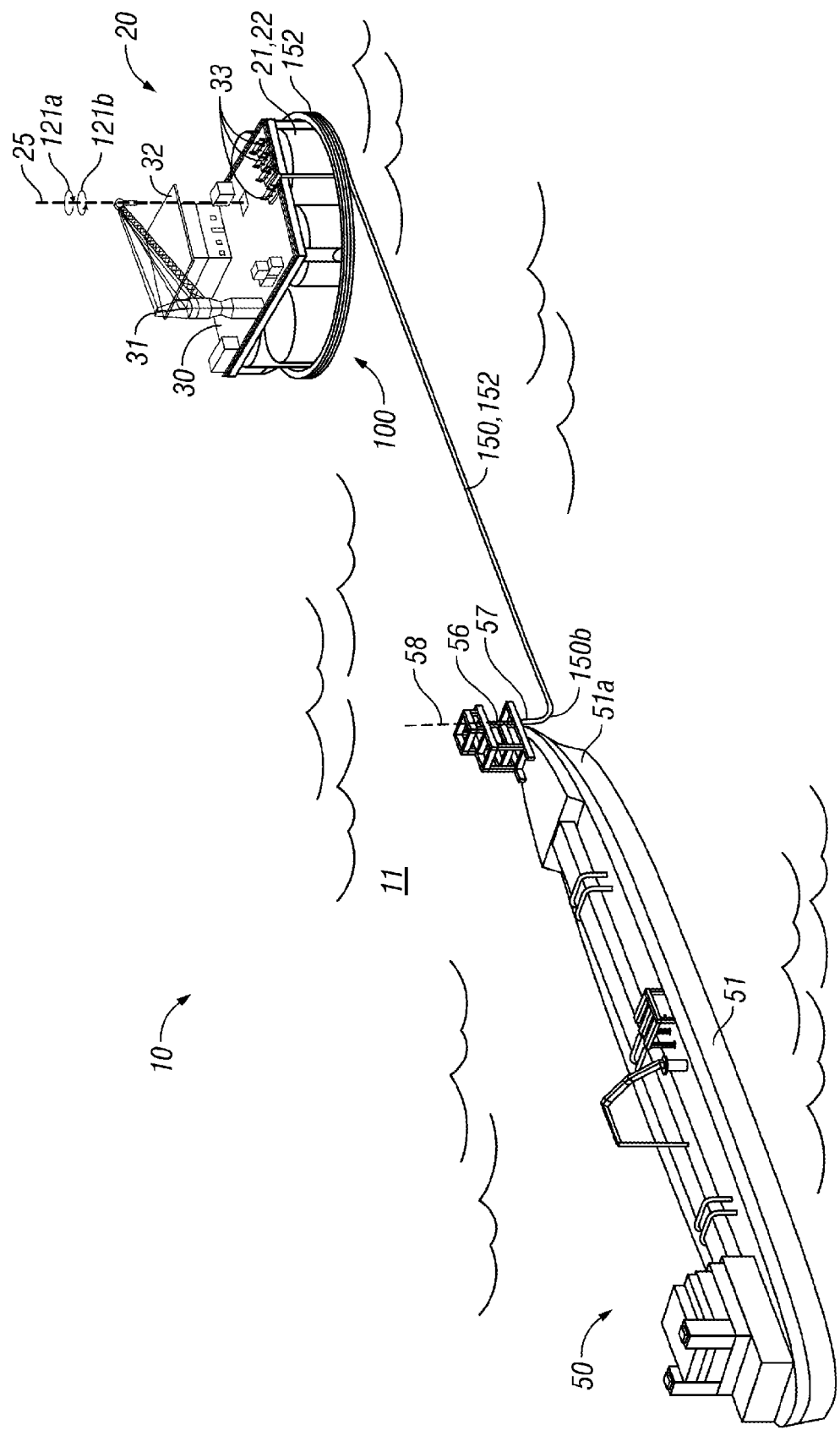
FIG. 2 is a perspective top view of the system of FIG. 1.

Referring now to FIGS. 1 and 2, a system 10 for the offshore transfer of a stored fluid is shown. System 10 includes an offshore fluid storage structure 20, an offshore transport vessel 50, and a fluid offloading system 100 that delivers fluid stored in structure 20 to vessel 50. In embodiments described herein, the fluid stored by structure 20 and delivered to vessel 50 with offloading system 100 is processed liquid oil. However, in general, any fluid (liquid, gas, or combination thereof) may be transferred from an offshore fluid storage structure (e.g., offshore structure 20) to an offshore transport vessel (e.g., vessel 50) with embodiments of offloading systems described herein (e.g., offloading system 100). As best shown in FIG. 2, offloading system 100 is positioned above the sea surface 11 and extends from structure 20 to vessel 50. As will be described in more detail below, offloading system 100 moors vessel 50 to storage structure 20, while simultaneously delivering fluid (e.g., oil) from storage structure 20 to vessel 50.

Figure 3:
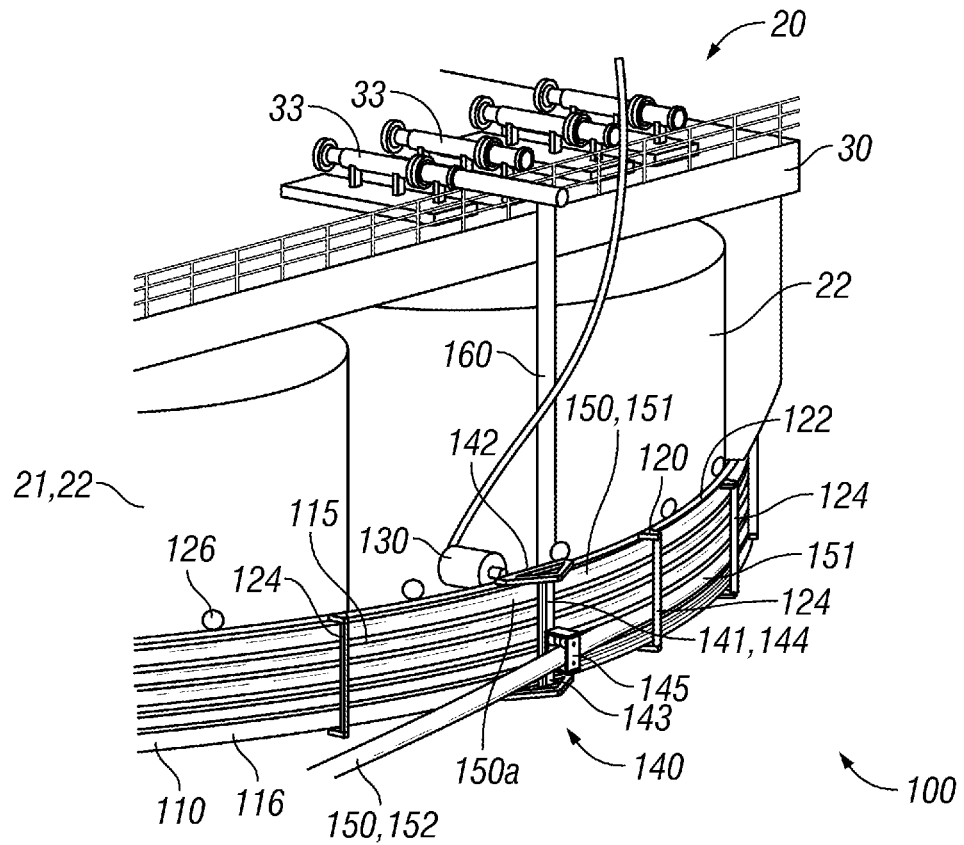
FIG. 3 is an enlarged partial perspective view of the offloading system of FIG. 1.

Referring still to FIGS. 1 and 2, in this embodiment, fluid storage structure 20 is a moored floating offshore structure including a buoyant hull 21 and a deck 30 mounted to hull 21. Hull 21 has a substantially vertical central or longitudinal axis 25 and comprises a plurality of buoyant vertical columns 22. Columns 22 are filled with air, sea water, stored fluid (e.g., oil), or combinations thereof. The buoyancy of columns 22, and hence the buoyancy of hull 21, may be controlled and adjusted by varying the relative volumes of air, water, and oil housed within columns 22. Deck 30 is coupled to and supported by hull 21 above the sea surface 11. In this embodiment, a crane 31 and a helipad 32 are disposed on deck 30, as well as various other pieces of equipment. As best shown in FIG. 3, storage structure 20 includes a plurality of fluid outlets 33 extending from deck 30. Outlets 33 are coupled to columns 22 and as will be described in more detail below, supply fluid stored in columns 22 to offloading system 100, which then delivers the fluid to vessel 50.

As best shown in FIG. 1, structure 20 is moored to the sea floor with a mooring system 40 including a plurality of mooring lines 41. Each line 41 has first or upper end 41a secured to hull 21 below the sea surface 11, and a second or lower end (not shown) secured to the sea floor with a pile or other suitable anchoring device. Mooring system 40 maintains the position of structure 20 at the sea surface 11 when structure 20 is subjected to wind and wave forces. It should be appreciated that offloading system 100 is disposed above mooring system 40 so that systems 40, 100 do not interfere with each other.

In general, storage structure 20 may be any type of moored floating structure or fixed structure configured to store fluids (e.g., oil) in an offshore environment including, without limitation, semi-submersible platform, a Spar platform, a tension leg platform, or a jackup platform. However, at offshore locations with an undeveloped or non-existent pipeline infrastructure, offshore structures that provide a relatively large storage volume such as semi-submersible platforms and Spar platforms are preferred. In this embodiment, structure 20 is a moored floating Spar platform that provides a relatively large fluid storage volume compared to other types of floating structures. In addition, the general cylindrical shape of a Spar is particularly suited for use with the annular components of the offloading system 100 described in more detail below. Since structure 20 stores and offloads oil in this embodiment, it may also be referred to as a Floating Production Storage and Offloading Unit (FPSO) or Floating Storage and Offloading Unit (FSO) depending on whether it (a) receives crude oil, processes the crude oil (e.g., removes water from the crude oil), and stores the processed oil for subsequent offloading to vessel 50 (FPSO); or (b) receives oil that has already been processed and stores the processed oil for subsequent offloading to vessel 50 (FSO). In this embodiment, structure 20 is a Spar FPSO.

Referring again to FIGS. 1 and 2, fluid transport vessel 50 is coupled and receives fluid (e.g., processed oil) from structure 20 via offloading system 100, and then disconnects from system 100 and transports the transferred fluid to other geographic location(s). In this embodiment, vessel 50 is an offshore tanker, and in particular, a Very Large Crude Carrier (VLCC) tanker that provides a relatively large fluid storage capacity and is suited for long range transoceanic transportation. Tanker 50 includes a hull 51, a deck 53 supported by hull 51, and a plurality of propellers or thrusters for moving tanker 50 through the water along the sea surface 11. Hull 51 defines a forward bow 51*a* and a rearward stern 51*b* opposite bow 51*a*. Tanker 50 also includes a fluid inlet 56 for receiving fluid from offloading system 100. In this embodiment, inlet 56 is position on the bow 51*a* of tanker 50 and comprises a swivel coupling 57 configured to allow tanker 50 to pivot or rotate about a vertical axis 58 relative to system 100 and structure 20 while fluid is delivered to tanker 50 from structure 20.

In this embodiment, tanker 50 is not moored to the sea floor, but is directly coupled and moored to storage structure 20 with system 100. As previously described, in this embodiment, tanker 50 is a VLCC tanker, which is typically not equipped with a Dynamic Positioning System (DPS) to maintain the position of tanker 50 relative to structure 20. Therefore, in this embodiment, tanker 50 is allowed to "weathervane" about storage structure 20. As is known in the art, the term "weathervane" as used in relation to offshore structures refers to the circumferential or rotational movement of a floating vessel on the sea surface about a point in response to changes in environmental conditions (e.g., wind, waves, currents, etc.).

Referring now to FIGS. 2 and 3, offloading system 100 simultaneously delivers fluid stored in structure 20 to tanker 50, moors tanker 50 to structure 20, and allows tanker 50 to weathervane about structure 20. In this embodiment, offloading system 100 comprises an annular conduit support structure 110 disposed about structure 20, an annular reel 120 disposed about structure 20 and rotatably coupled to support structure 110, and a flexible flowline or conduit 150 at least partially wound about support structure 110.

Figure 4:
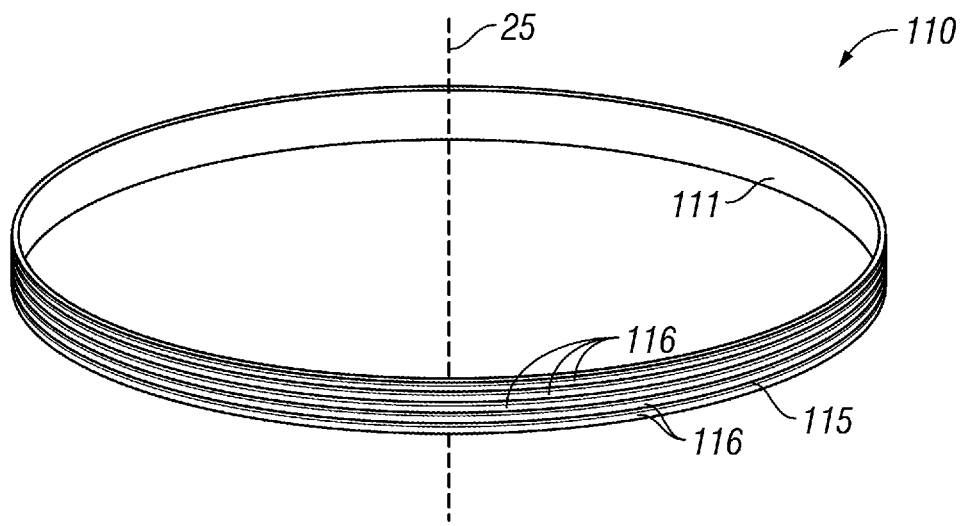
FIG. 4 is a perspective view of the conduit support structure of FIG. 3.
Figure 5:
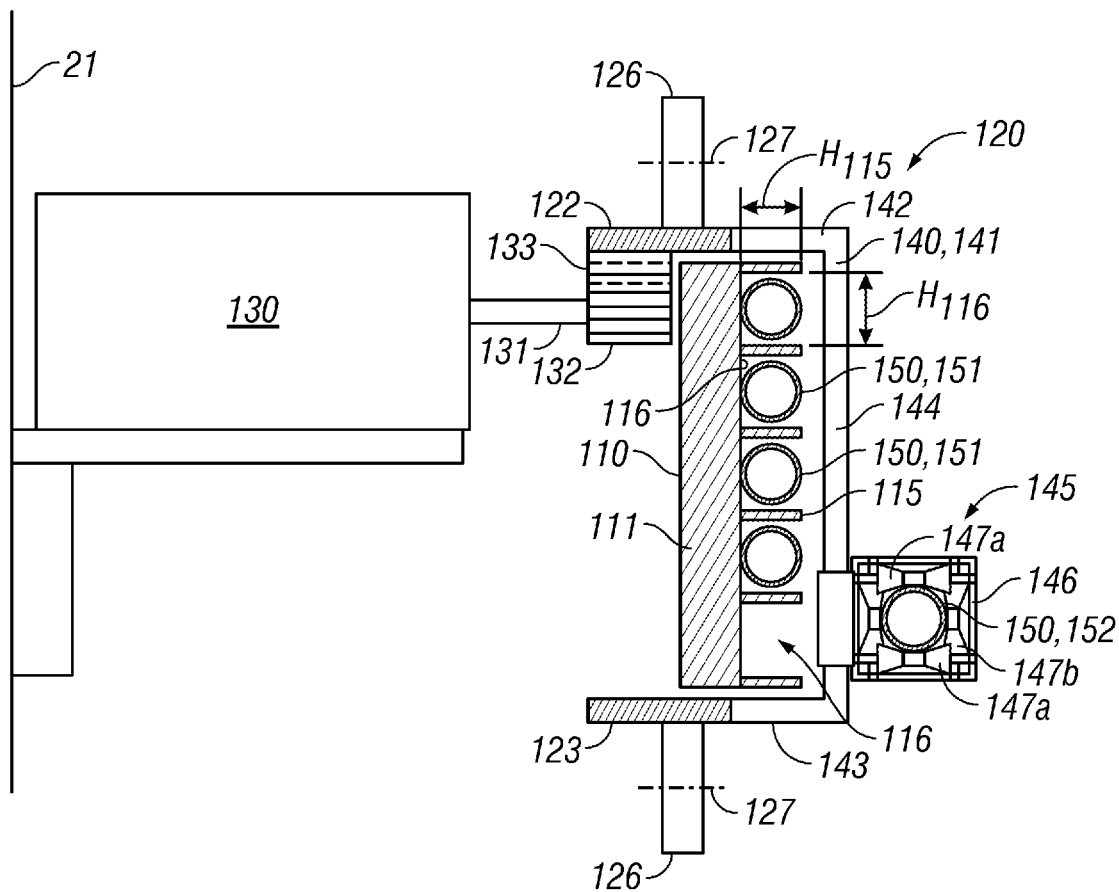
FIG. 5 is a cross-sectional view of the offloading system of FIG. 3.

Referring now to FIGS. 3-5, conduit support structure 110 is coaxially aligned with structure 20 and secured to hull 21 such that it does not move translationally or rotationally relative to hull 21. In this embodiment, support structure 110 includes a cylindrical base 111 and a helical rib or divider 115. Divider 115 extends helically about the radially outer surface of base 111. In this embodiment, divider 115 makes a plurality of axially spaced helical turns about base 111, thereby defining a helical recess 116 extending along the radially outer surface of support structure 110. Recess 116 is sized to receive flexible conduit 150. In particular, recess 116 has a uniform axial height $H_{116}$ equal to or slightly greater than the diameter of flexible conduit 150. In addition, divider 115 axially supports any portion of conduit 150 seated within recess 116. Thus, divider 115 preferably has a height $H_{115}$ measured radially outward from base 111 that is equal to or greater than the radius of conduit 115. To reduce the likelihood of flexible conduit 150 getting damaged or kinked when it is wrapped around support structure 110 and seated in recess 116, conduit support structure 110 preferably has an inner radius of at least 20 feet. Although support structure 110 is shown and described as having a continuous annular shape, in other embodiments, the support structure for supporting the flexible conduit (e.g., support structure 110) may be formed form a plurality of circumferentially adjacent arcuate panels disposed about the offshore fluid storage structure (e.g., structure 20).

Referring now to FIGS. 3 and 5, reel 120 is coaxially aligned with structure 20 and is rotatably coupled to hull 21 and support structure 110 such that reel 120 may be rotated about axis 25 in a first direction 121*a* and a second direction 121*b* opposite first direction 121*a* (FIGS. 1 and 2). Reel 120 is employed to wind flexible conduit 150 around support structure 110 (i.e., pay in conduit 150) when rotated in the first direction 121*a* and unwind flexible conduit 150 from support structure 110 (i.e., pay out conduit 150) when rotated in the second direction 121*b*. In this embodiment, reel 120 includes an upper annular member or ring 122, a lower annular member or ring 123 axially positioned below upper ring 122, and a plurality of circumferentially spaced connecting members or struts 124 extending axially between rings 122, 123. Each ring 122, 123 is oriented generally horizontally, with struts 124 extending vertically therebetween. Struts 124 maintain the axial spacing of rings 122, 123 and enhance the rigidity of reel 120.

As best shown in FIG. 5, in this embodiment, reel 120 is supported by a plurality of circumferentially-spaced rollers 126 that facilitate the rotation of reel 120 about axis 25 relative to support structure 110 and hull 21. Each roller 126 is rotatably coupled to hull 21 and is free to rotate in a clockwise or counterclockwise direction about a central rolling axis 127. A projection of each axis 127 intersects axis 25. A first or upper set of circumferentially-spaced rollers 126 are positioned axially above and rotatably engage upper ring 122 and a second set of circumferentially-spaced rollers 126 are positioned axially below and rotatably engage lower ring 123.

Referring still to FIGS. 3 and 5, reel 120 also includes a conduit guide assembly 140 that guides flexible conduit 150 into recess 116 during rotation of reel 120 in first direction 121*a* during pay in, and guides flexible conduit 150 as it extends from support structure 110 during rotation of reel 120 in second direction 121*b* during pay out. Guide assembly 140 includes a support bracket 141 and conduit guide member or fairlead 145 moveably coupled to support bracket 141. As best shown in FIG. 5, support bracket 141 has a generally C-shaped cross-section includes an upper connecting member 142 extending radially outward from upper ring 122, a lower connecting member 143 extending radially outward from lower ring 123 and circumferentially aligned with upper connecting member 32142, and a cross-member 144 extending axially between members 142, 143. Fairlead 145 is moveably coupled to cross-member 144 and is configured to move axially up and down along cross-member 144. In general, any suitable means may be used to movably couple fairlead 145 along cross-member 144. For example, fairlead 145 may include a sleeve that slidingly engages cross-member 144. Further, guide 145 may be allowed to move freely along cross-member 144 or powered to move up or down along cross-member 144. For example, fairlead 145 may include a motor driven gear that positively engages a rack mounted to cross-member 144.

Referring still to FIGS. 3 and 5, reel 120 also includes a conduit guide assembly 140 that guides flexible conduit 150 into recess 116 during rotation of reel 120 in first direction 121a during pay in, and guides flexible conduit 150 as it extends from support structure 110 during rotation of reel 120 in second direction 121b during pay out. Guide assembly 140 includes a support bracket 141 and conduit guide member or fairlead 145 moveably coupled to support bracket 141. As best shown in FIG. 5, support bracket 141 has a generally C-shaped cross-section includes an upper connecting member 142 extending radially outward from upper ring 122, a lower connecting member 143 extending radially outward from lower ring 123 and circumferentially aligned with upper connecting member 132, and a cross-member 144 extending axially between members 142, 143. Fairlead 145 is moveably coupled to cross-member 144 and is configured to move axially up and down along cross-member 144. In general, any suitable means may be used to movably couple fairlead 145 along cross-member 144. For example, fairlead 145 may include a sleeve that slidingly engages cross-member 144. Further, guide 145 may be allowed to move freely along cross-member 144 or powered to move up or down along cross-member 144. For example, fairlead 145 may include a motor driven gear that positively engages a rack mounted to cross-member 144.

Figure 6:
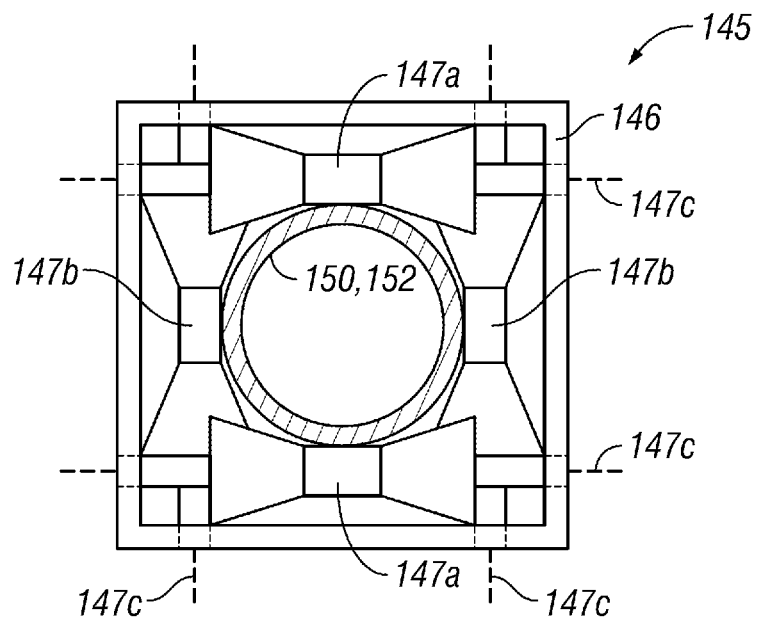
FIG. 6 is an end view of the conduit guide of the offloading system of FIG. 3.

Referring now to FIGS. 5 and 6, in this embodiment, fairlead 145 includes a rectangular frame 146, a pair of axially spaced rollers 147a extending horizontally across the inside of frame 146, and a pair of radially spaced rollers 147b extending vertically across the inside of frame 146. Each roller 147a, b is free to rotate about its corresponding rotational axes 147 relative to frame 146 and conduit 150. Axes 147c of rollers 147a are oriented perpendicular to axis 25, and generally oriented such that a projection of axes 147c of rollers 147a intersect axis 25. Axes 147c of rollers 147b are oriented parallel to axis 25. One roller 147a is positioned axially above conduit 150 extending through fairlead 145 and the other roller 147a is positioned axially below conduit 150 extending through fairlead 145; and one roller 147b is positioned radially inside conduit 150 extending through fairlead 145 and the other roller 147b is positioned radially outside conduit 150 extending through fairlead 145. Each roller 147a, b engages conduit 150 and rolls along conduit 150 as it moves through fairlead 145. As shown in the front view of FIG. 6, vertical rollers 147b are positioned behind horizontal rollers 147a. However, rollers 147a, b are preferably spaced apart a sufficient distance to allow conduit 150 to extend therebetween without compressing or squeezing conduit 150. Thus, in this embodiment, the minimum axial distance between rollers 147a and the minimum radial distance between rollers 147b is each preferably greater than the diameter of conduit 150.

Figure 7:
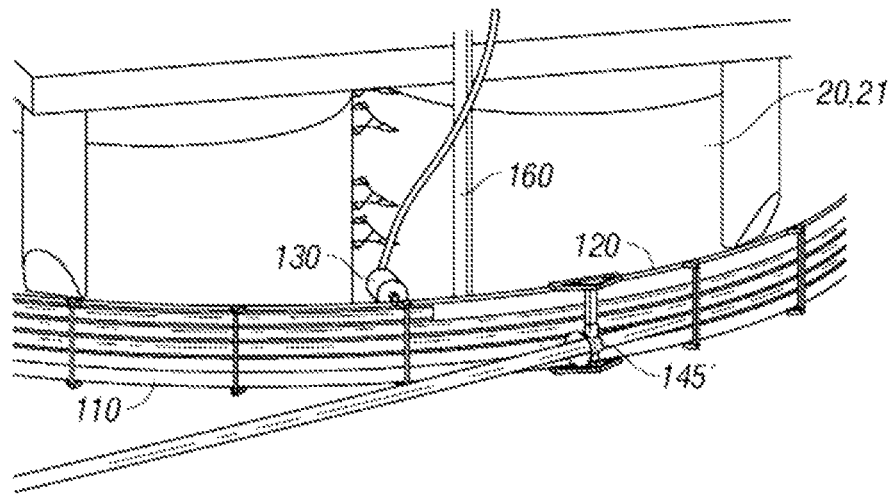
FIG. 7 is a perspective view of an embodiment of an offloading system for transferring a stored fluid from the moored offshore structure to the transport vessel of FIG. 1.
Figure 8:
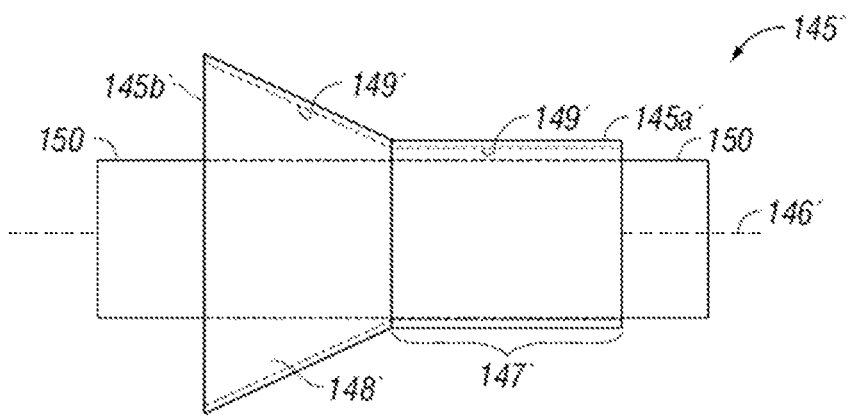
FIG. 8 is a side view of the conduit guide of the offloading system of FIG. 7.
Figure 9:
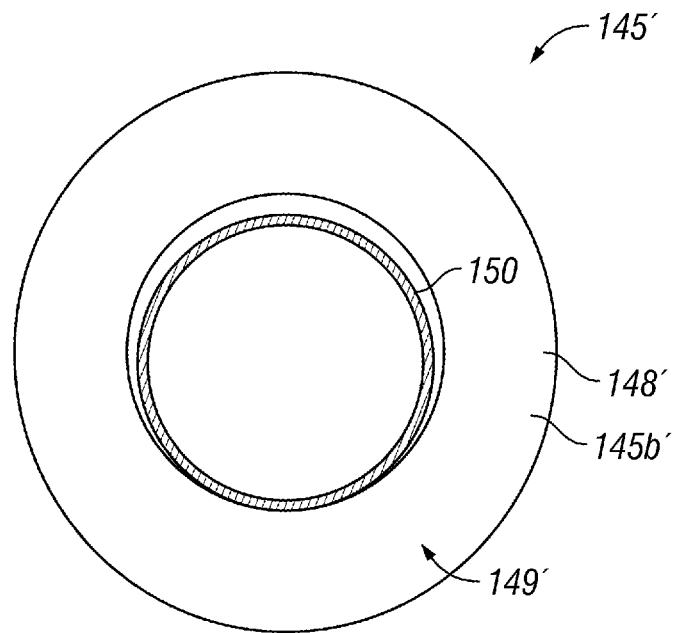
FIG. 9 is an end view of the conduit guide of the offloading system of FIG. 7.

Referring briefly to FIGS. 7-9, an alternative embodiment a fairlead 145' that may be used in the place of fairlead 145 previously described is shown. In this embodiment, fairlead 145' comprises a generally bell-shaped tubular having a central axis 146', a first end 145a', a second end 145b' opposite end 145a', a first cylindrical section 147' extending axially from end 145a', and a second frustoconical section 148' extending axially from end 145b' to section 147'. Sections 147', 148' define a throughbore 149' extending axially between ends 145a' and 145b'. Conduit 150 extends through bore 149' and slidingly engages sections 147', 148'. Thus, bore 149' preferably has a minimum diameter greater than the diameter of conduit 150.

Referring again to FIGS. 1-3, flexible conduit 150 has a first or inlet end 150a and a second or outlet end 150b. A rigid fluid supply conduit 160 extends between one fluid outlet 33 and inlet end 150a, thereby supplying stored fluid from structure 20 to conduit 150. Outlet end 150b is connected to swivel coupling 57 of tanker 50. Thus, fluid stored in storage structure 20 is delivered through outlet 33 and conduits 160, 150 to tanker inlet 56.

Since conduit 150 may be wound or unwound from support structure 110, conduit 150 may be described as having a first portion 151 extending from inlet end 150a and coiled around support structure 110 within helical recess 116, and a second portion 152 extending from first portion 151 and support structure 110 to tanker 50. Second portion 152 is not wrapped around support structure 110, but rather, extends generally tangentially from support structure 110 through fairlead 145 to tanker 50.

As will be described in more detail below, flexible conduit 150 both delivers fluid between storage structure 20 and tanker 50 and moors tanker 50 to structure 20. In particular, flexible conduit 150 is placed in tension between structure 20 and tanker 50. Accordingly, flexible conduit 150 preferably comprises a flexible hose or riser having strength to withstand the anticipated tensile mooring loads as well as pressure ratings (at least 200 bar) to withstand the anticipated pressure of the fluid flowing therethrough during offloading operations. Examples of suitable conduits include, without limitation, flexible flowlines and risers available from Technip-Coflexip of Houston, Tex., Wellstream International Ltd. of Houston, Tex., and NKT Flexibles of Broendby, Denmark.

Figure 10:
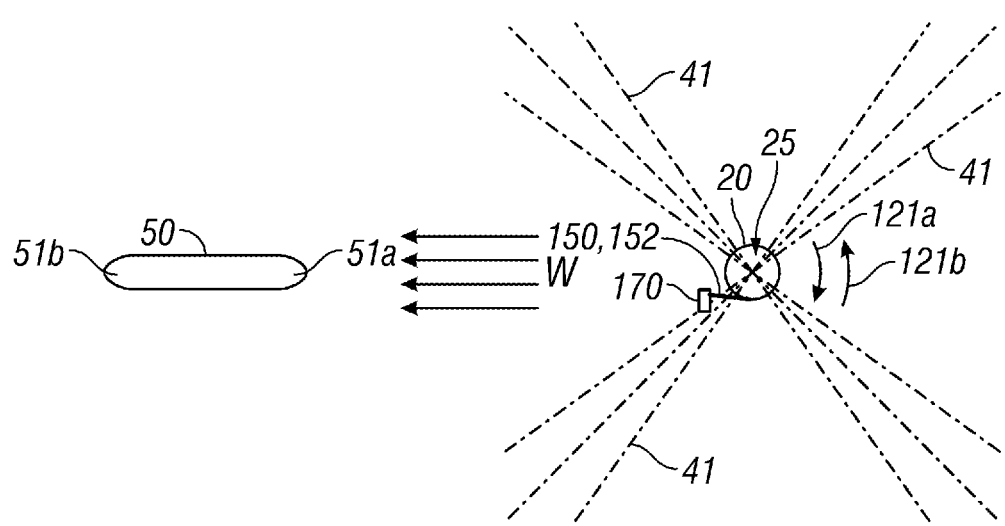
FIGS. 10 to 13 are sequential schematic top views illustrating the deployment of the conduit of the offloading system of FIGS. 1-3.

Referring now to FIGS. 10-13, the deployment of flexible conduit 150 for offloading stored fluids from offshore structure 20 to tanker 50 is schematically shown. As shown in FIG. 10, tanker 50 is first positioned at a safe distance from structure 20 to reduce the likelihood of a collision, and orients itself in a direction generally into the wind and waves, generally represented by "W" in FIGS. 10-13. With tanker 50 facing into the wind and waves W, thrusters are employed to maintain the position of tanker 50 and distance from structure 20. With tanker 50 positioned at a suitable distance from structure 20, a relatively small assist vessel 170 is employed to unspool a portion of flexible conduit 150 (e.g., second portion 152) from support structure 110. In particular, outlet end 150b of conduit 150 is coupled to assist vessel 170 such as with a swivel connector, and assist vessel 170 begins to move circumferentially about storage structure 20 in second direction 121b to unwind a portion of conduit 150 from support structure 110.

Figure 11:
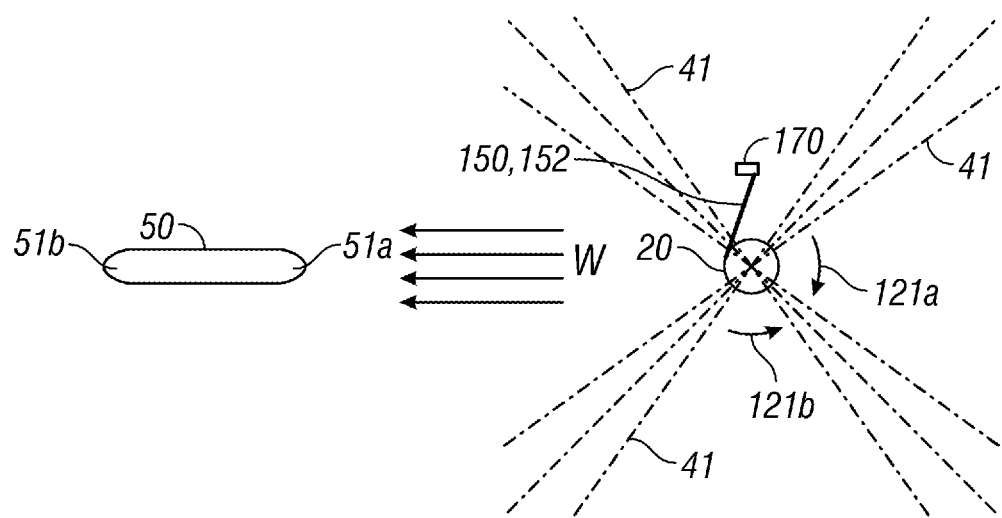
Figure 12:
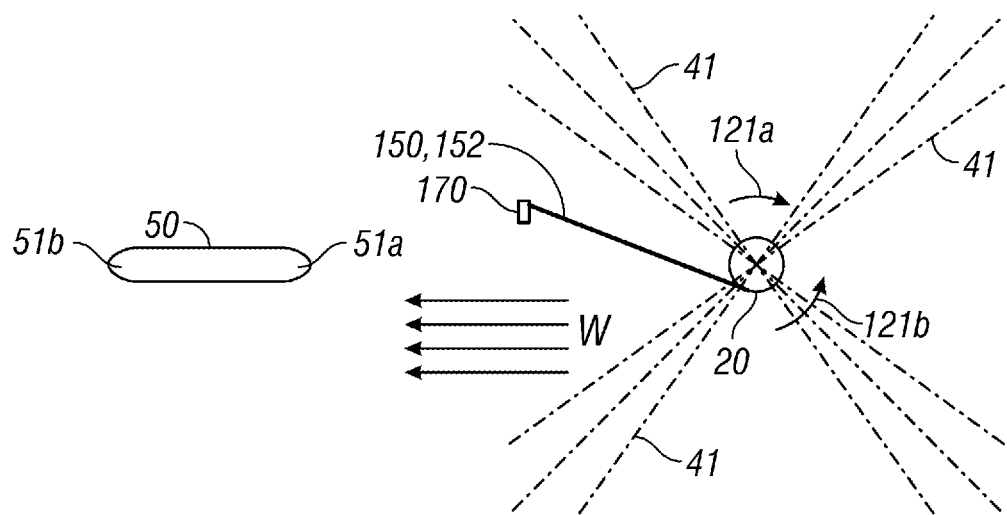
Figure 13:
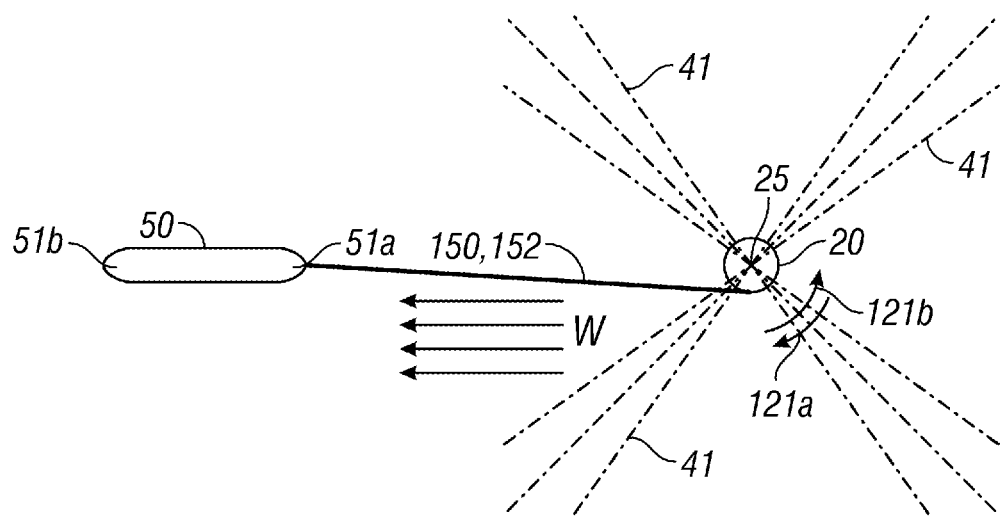

As shown in FIGS. 10 and 11, as vessel 170 moves about structure 20, it pulls second portion 152 radially outward, which urges fairlead 145 and reel 120 in second direction 121b, thereby allowing conduit 150 to be paid out through fairlead 145 generally tangent to structures 20, 110. During pay out of conduit 150, shaft 131 of motor 130 is preferably allowed to rotate freely in response to the rotation of reel 120. In other words, the rotation of reel 120 in second direction 121b is preferably not inhibited by motor 130. In other embodiments, motor 130 may be employed to aid in the rotation of reel 120 in second direction. As vessel 170 moves circumferentially about storage structure 20 in second direction 121b and reel 120 moves in second direction 121b, the length of second portion 152 of conduit 150 (i.e., the length of the portion of conduit 150 unwound from support structure 110) increases. Thus, vessel 170 may simultaneously move radially outward from structure and circumferentially in second direction 121b about structure 20. Moving now to FIG. 13, this process is continued until the length of second portion 152 is sufficient to couple outlet end 150b to swivel coupling 57 of tanker 50 with tanker 50 at a safe distance from structure 20. With outlet end 150b securely coupled to swivel coupling 57, thrusters 54 are preferably operated in reverse to place conduit 150 in tension, thereby mooring tanker 50 to storage structure 20 with conduit 150. Next, fluid (e.g., oil) stored in structure 20 may be pumped through conduit 150 to tanker 50.

Figure 14:
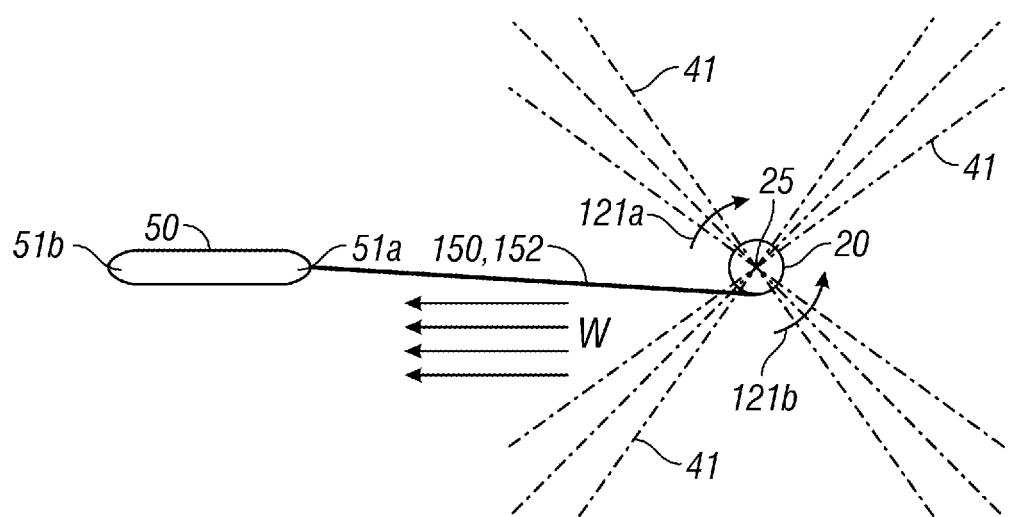
FIGS. 14 and 15 are sequential schematic top views illustrating the weathervaning of the transport vessel about the moored offshore storage structure of FIGS. 10-13 in response to changes in environmental conditions and while offloading stored fluid from the storage structure to the transport vessel.
Figure 15:
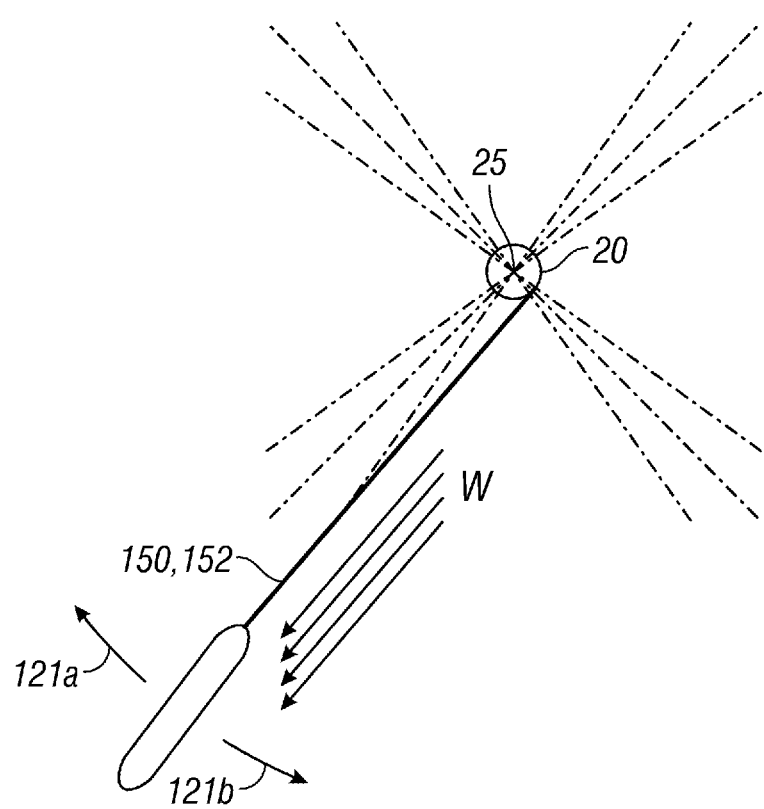

Referring to FIGS. 14 and 15, during fluid offloading operations, tanker 50 is free to weathervane circumferentially about storage structure 20 in response to changes in the direction of the wind and waves W. For example, moving from FIG. 14 to FIG. 15, the direction of wind and waves W change direction and tanker 50 moves in response, while maintaining an orientation generally facing into the wind and waves W and tension on conduit 150. As tanker 50 moves circumferentially about structure 20 in either direction 121a, b, conduit 150 is wound or unwound from support structure 110 with the aid of reel 120.

Once offloading is complete, outlet end 150b of conduit 150 is disconnected from swivel coupling 57 of tanker 50, and reel 120 is rotated by motor 130 in first direction 121a to wind conduit 150 around support structure 110. Assist vessel 170 may be employed to aid in the pay in operations.

In the manner described, embodiments described herein allow offloading of an offshore fluid storage structure (e.g., structure 20) to a tanker (e.g., tanker 50) without the use of a complex turret or intermediate offloading buoy. In addition, since the tanker is moored to the storage facility during offloading operations and allowed to weathervane about the storage facility without interference from other lines (e.g., mooring lines) or equipment, a DPS system is not required.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. OR

What is claimed is:

1. A system for offloading a fluid from an offshore fluid storage structure, comprising:
   an annular conduit support structure disposed about and around the offshore fluid storage structure, wherein the support structure is non-rotatably coupled to the offshore fluid storage structure;
   an annular reel disposed about and around the offshore fluid storage structure, wherein the reel is rotatably coupled to the support structure and is configured to rotate relative to the conduit support structure and the offshore fluid storage structure, and wherein the reel includes a conduit fairlead configured to move relative to the support structure; and
   a flexible conduit having a fluid inlet end and a fluid outlet end, wherein the flexible conduit includes a first portion wrapped around the conduit support structure and a second portion extending from the conduit support structure through the fairlead.

2. The system of claim 1, wherein the conduit support structure comprises a cylindrical base and a divider extending helically about the base.

3. The system of claim 2, wherein the base and the divider define a helical recess extending about the conduit support structure.

4. The system of claim 3, wherein the first portion of the conduit is disposed in the helical recess.

5. The system of claim 3, wherein the helical recess has a width W measured axially between a pair of axially adjacent turns of the divider, wherein width W is equal to or greater than a diameter of the flexible conduit.

6. The system of claim 1, wherein the reel comprises an upper annular member disposed about and around the offshore fluid storage structure, a lower annular member disposed about and around the offshore fluid storage structure below the upper annular member, and a cross-member extending axially from the upper annular member to the lower annular member, wherein the fairlead is moveably coupled to the cross-member.

7. The system of claim 6, wherein the reel is supported by a plurality of circumferentially-spaced rollers disposed about the offshore fluid storage structure.

8. The system of claim 7, wherein a first set of the plurality of circumferentially-spaced rollers rotatably engage the upper annular member and a second set of the plurality of circumferentially-spaced rollers rotatably engage the lower annular member.

9. The system of claim 6, further comprising a motor fixably coupled to the offshore fluid storage structure and configured to rotate the reel relative to the support structure in a first direction.

10. The system of claim 1, wherein the flexible conduit is a flexible riser.

11. A system, comprising:
    a floating offshore fluid storage structure moored to the sea floor with a plurality of mooring lines, wherein the floating offshore fluid storage structure includes a buoyant hull having a substantially vertical central axis and a deck mounted to the buoyant hull;
    an annular conduit support structure disposed about and around the offshore fluid storage structure, wherein the support structure is non-rotatably coupled to the offshore fluid storage structure;
    an annular reel disposed about and around the offshore fluid storage structure, wherein the annular reel is rotatably coupled to the support structure and is configured to rotate relative to the support structure and the offshore fluid storage structure;
    a tanker spaced apart from the floating offshore fluid storage structure;
    a flexible conduit extending from the conduit support structure to the tanker, wherein the conduit has an inlet end coupled to the floating offshore fluid storage structure, an outlet end pivotally coupled to the tanker, a first portion extending from the inlet end, and a second portion extending from the first portion and the floating offshore fluid storage structure to the outlet end;
    wherein the first portion is coiled around the conduit support structure, and Wherein the first portion is disposed about the central axis of the buoyant hull and an outer perimeter of the buoyant hull of the floating offshore fluid storage structure.

12. The system of claim 11, wherein the flexible conduit is a flexible riser having a diameter between 10 and 20 in.

13. The system of claim 11, wherein the first portion of the flexible conduit is seated in a helical recess extending along the outer surface of the conduit support structure.

14. The system of claim 13, wherein the reel includes a conduit guide member configured to move up and down relative to the support structure, wherein the flexible conduit extends through the guide.

15. The system of claim 13, wherein the conduit support structure has a radius of at least 20 feet.

16. The system of claim 13, further comprising at least one motor configured to rotate the reel relative to the conduit support structure and the floating offshore fluid storage structure.

17. The system of claim 11, wherein the first portion of the flexible conduit extends a plurality of times about the outer perimeter of the hull of the floating offshore fluid storage structure.

18. The system of claim 11, wherein the tanker is a VLCC tanker without a dynamic positioning system.

19. The system of claim 11, wherein the tanker is moored to the floating offshore fluid storage structure by the flexible conduit.

20. The system of claim 1, wherein the offshore fluid storage structure is a floating offshore fluid storage structure including a buoyant hull.

21. The system of claim 11, wherein the floating offshore fluid storage structure includes a buoyant hull.

* * * * *